United States Patent [19]
Mooney et al.

[11] Patent Number: 6,072,100
[45] Date of Patent: Jun. 6, 2000

[54] EXTRUDABLE COMPOSITIONS FOR TOPICAL OR TRANSDERMAL DRUG DELIVERY

[75] Inventors: Mark T. Mooney, Somerville; Michael T. Schiraldi, East Brunswick, both of N.J.

[73] Assignee: Johnson & Johnson Consumer Products, Inc., Skillman, N.J.

[21] Appl. No.: 09/014,779

[22] Filed: Jan. 28, 1998

[51] Int. Cl.[7] ................................................. A61M 31/00
[52] U.S. Cl. .............................. 602/48; 602/43; 604/307; 424/448
[58] Field of Search ................................... 602/8, 41, 44, 602/48, 45; 604/307; 424/448

[56] References Cited

U.S. PATENT DOCUMENTS

| | | | |
|---|---|---|---|
| 4,713,243 | 12/1987 | Schiraldi et al. | 424/151 |
| 4,880,416 | 11/1989 | Horiuchi et al. | 604/37 |

*Primary Examiner*—John G. Weiss
*Assistant Examiner*—Kelvin E Hart
*Attorney, Agent, or Firm*—Lawerence D. Schuler; Frederick L. Herman

[57] ABSTRACT

An effective and convenient medicament delivery system comprising novel extrudable compositions. The preferred compositions of the invention contain a thermoplastic water-soluble polymer selected from the group consisting of hydroxypropyl cellulose and polyethylene oxide; a water-soluble polymer derived from acrylic acid; medicament; and plasticizer. The compositions provide an effective medicament delivery system and are especially suitable for use with adhesive bandages.

39 Claims, 1 Drawing Sheet

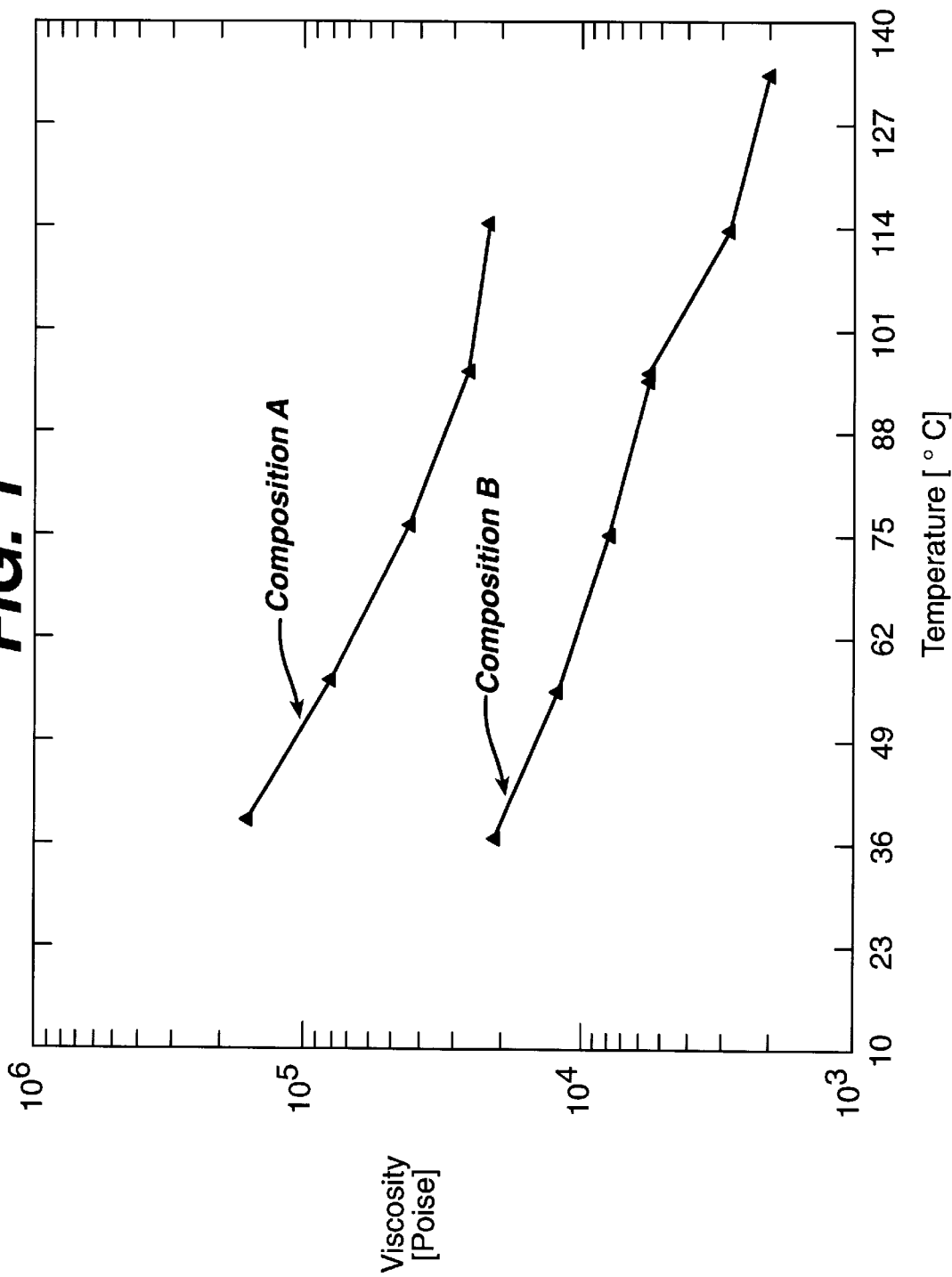

EXTRUDABLE COMPOSITIONS FOR TOPICAL OR TRANSDERMAL DRUG DELIVERY

BACKGROUND OF THE INVENTION

This invention relates to novel extrudable compositions for the topical application of medicaments to human or animal skin and, more particularly, to bandages containing such compositions. Adhesive bandages, wound dressings, and the like containing the novel compositions of the invention provide a superior wound care system.

Creams, ointments, solutions and powders are known to be useful for the topical application of various drugs to skin. However, the application of these materials typically is non-quantitative and it is difficult for the user to control the amount of drug delivered to the area to be treated. When such materials are used in conjunction with adhesive bandages or wound dressings, they frequently detackify (that is, result in a loss of adhesion) the adhesive portion of the bandage, thereby increasing the risk of contamination. In addition, such materials are messy and inconvenient to use, frequently soiling clothing and the like.

Various wound dressings and bandages for the topical application of medicaments are also known. For example, U.S. Pat. No. 4,616,644, issued Oct. 14, 1986 in the name of Saferstein et al., describes an adhesive bandage wherein a thin coating of a high molecular weight polyethylene oxide is applied to the surface of the wound release cover of the bandage to stop bleeding faster.

U.S. Pat. No. 4,880,416, issued Nov. 14, 1989 in the name of Horiuchi et al. describes a dermal bandage comprised of a film-like adhesive material that comprises vinyl acetate polymer and a polycarboxylic acid or anhydride.

In EPO Application 0297828, Charkoudian et al. describes a bandage which is coated or impregnated with a soft, waxy, low melting composition containing a medicament. In example 1 a solution of polyethylene glycol and benzocaine is coated onto a nonwoven fabric of the type used in bandages. In example 2 Charkoudian et al. further describes impregnating a non-woven fabric with a methanol solution of polyvinyl pyrrolidone (PVP), polyethylene glycol and benzocaine, and letting the methanol evaporate. The resulting composition is extremely tacky and dissolves very slowly upon contact with wound exudate. Moreover, since the compositions have melting points below 40° C., they cannot be subject to conventional ethylene oxide sterilization techniques.

In U.S. Pat. No. 4,713,243, issued Dec. 15, 1987, Schiraldi et al. describes a bioadhesive extruded film that is useful in intra-oral drug delivery. The thin film is comprised of a bioadhesive layer consisting essentially of 40–95% by weight hydroxypropyl cellulose, 5–60% of a homopolymer of ethylene oxide, 0–10% of a water insoluble polymer, and 2–10% of a plasticizer.

From the foregoing discussion, it will be seen that various compositions and devices useful for topically applying medicaments to the skin are known. However, such compositions have not been found to be entirely suitable when used by themselves or in connection with conventional adhesive bandages. For example, many compositions interfere with a bandage's functions to absorb wound exudate and adhere to the skin. Another problem is that upon dissolution many of these materials form a thin, free-flowing fluid having little structural integrity. As a result, the medicament is dispersed too quickly and readily spreads away from the area to be treated. Yet another problem is that many compositions of the prior art are not stable at higher temperatures and humidities. This property is crucial because the compositions may be stored for lengthy periods under less than ideal warehouse conditions. In addition, they must be able to withstand rigorous sterilization procedures.

Accordingly, it is an object of the present invention to provide a method for topically or transdermally delivering a medicament which comprises applying to the skin a novel, extrudable composition which, upon contact with body fluid, releases a controlled amount of medicament to the area to be treated.

It is another object of the invention to provide an extrudable composition for delivering a medicament to the skin which can be used alone or in conjunction with sterilized and/or adhesive bandages.

It is yet another object of the invention to provide a composition which does not readily dissolve to a free-flowing fluid upon contact with body fluids.

It is a further object of the invention to provide an extruded film that is an effective and convenient medicament delivery system.

SUMMARY OF THE INVENTION

The inventors have found that various extrudable compositions comprising:

(a) at least one thermoplastic water-soluble polymer;

(b) at least one water-soluble polymer derived from carboxylic acid;

(c) plasticizer; and (d) at least one medicament, can achieve the above objects and advantages.

The inventors have further found that extrudable compositions comprising, about 5–70% by weight of (a); about 1–10% of (b); about 10–80% of (c); and about 0.01–10% of (d), are particularly advantageous. In one preferred group of compositions, (a) comprises at least one polymer selected from the group consisting of hydroxypropyl cellulose and polyethylene oxide, (b) comprises at least one polymer derived from acrylic acid and (c) comprises at least one plasticizer selected from the group consisting of glycerine, propylene glycol and polyethylene glycol. The medicament comprises at least one, and preferably more, pharmaceutically acceptable therapeutic agents.

The compositions of this invention have the consistency of a non-flowing "ointment", as defined in *The United States Pharmacopeia, The National Formulary* (USP XXII, NF XVII), U.S. Pharmacopeial Convention, Inc., Rockville, Md., p. 1692 (1990), which is hereby incorporated by reference. After contact with body fluids, the composition dissolves into a matrix and releases the medicament, but it still possess good structural integrity.

The compositions of the invention can be placed directly on the skin as a free, extruded, single or multi-layered thin film. Alternatively, the films may be used in conjunction with a substrate like a bandage, wound dressing or blemish patch. For example, the absorbent pad material of a conventional bandage can be coated or at least partially impregnated with the composition, thereby providing a superior wound care product that rapidly delivers moisture-sensitive active ingredients to the area to be treated. Since the composition is extrudable, it can be formed into free films or coated on a substrate without the use of organic solvents.

In another preferred embodiment of the invention the novel extrudable compositions of the invention comprise:

(a) about 20–30% (by weight) of hydroxypropyl cellulose and about 0–10% of polyethylene oxide;

(b) about 1–10% by weight of a copolymer of acrylic acid and allyl sucrose;

(c) about 60–70% by weight of at least one plasticizer selected from the group consisting of glycerin and polyethylene glycol; and (d) about 0.01–10% by weight of medicament.

The novel extrudable compositions of the present invention alleviate many of the above problems. For example, when used in connection with an adhesive bandage, they do not interfere with the bandage's absorption and adhesion functions. In addition, they may be stored for at least one week at 40° C. and 80% relative humidity without experiencing a significant weight loss (i.e., more than 10% by weight). Moreover, the compositions and their properties are not impaired by ethylene oxide sterilization at 170° F., or E-beam or cobalt sterilization techniques. In addition, they are also sufficiently flexible so that they are comfortable to wear.

In another preferred embodiment of the invention, the extrudable compositions are used in conjunction with blemish patches to provide anti-acne medicament thereto.

BRIEF DESCRIPTION OF THE DRAWINGS

FIG. 1 is a graph showing the relationship between viscosity and temperature for a typical composition of the present invention and a comparative composition.

DETAILED DESCRIPTION OF THE INVENTION

The present invention is directed toward water-soluble films which rapidly dissolve in body fluids such as blood, perspiration, or wound exudate, and deliver active ingredients to a treatment site in a controlled manner.

In accordance with one embodiment of the present invention, the absorbent component of a bandage or wound dressing of known construction is coated or at least partially impregnated with the extrudable composition of the invention. Upon application to the injured area, the exudate from the wound or moisture from the skin dissolves the film, thereby converting it to a matrix having an ointment-like consistency and making the active ingredient available to treat the injury. Because of these ointment-like properties, the film is tacky and adheres to the skin.

As previously mentioned, the bandages or wound dressings which can be used in conjunction with the present invention comprise conventional adhesive or non-adhesive bandages or wound dressings of the medical or surgical type. Generally such bandages include a plastic film backing having attached thereto an absorbent pad portion. The absorbent pad material may be any of the woven or non-woven fabrics of natural or synthetic fibers heretofore employed as dressings, including for example, cotton, nylon or polyester. Suitable substrates further include woven or standard papers, and plastics. Preferred substrates include absorbent pad materials comprised of a rayon and polypropylene (10:90 weight ratio) spun bonded web, a knitted polyester fabric such as that used for DERMICEL taffeta tape manufactured by Johnson & Johnson Consumer Products, Inc., Skillman, N.J., and a composite nonwoven fabric made of thin, breathable polyester/polyurethane laminate known as FABRELLE which is manufactured by Fabrite Industries, Woodbridge, N.J.

Suitable plastic film backings include highly plasticized polyvinyl chloride, polyurethane, polyolefins, ethylene vinyl acetate and block copolymers films such as HYTREL® copolyester ether elastomers available from E. I. DuPont, Wilmington, Del. These plastic films may or may not contain an adhesive, which may or may not be pressure sensitive.

Adhesive bandages further include one or more release tabs. Release tabs (such as silicone-coated release paper or other alternate materials which can be readily removed at the time of use), are applied so as to cover, in an overlaying manner, the entire adhesive side of an adhesive bandage.

In addition, each bandage can be packaged and sealed in an individual wrapper (which typically is made of glassine-paper or a similar bacterial barrier material). Each bandage is packaged before it undergoes ethylene oxide or irradiation sterilization so as to maintain sterility until the bandage is ready for use.

In another preferred embodiment of the invention, the extrudable compositions may be used in conjunction with blemish patches to treat acne. Generally such blemish patches resemble the conventional adhesive bandages described above, i.e., they comprise a plastic film or fabric backing, an absorbent pad, an adhesive, and one or more release tabs, with the extrudable composition laminated to the absorbent pad.

As an alternate configuration, the blemish patch may simply contain a layer of the extrudable composition laminated to the aforementioned absorbent pad material. The extrudable composition serves as the media for holding the anti-acne medicament as well as an adhesive for adhering the patch to the skin site. Preferably, the pad stock will have some flexibility so that it conforms to facial contours. The patch may also contain a plastic film on the side of the pad opposite to the layer of extrudable composition to control moisture vapor transmission through the patch. A thin polyurethane film will allow for high moisture vapor transmission, whereas a thin polyolefin film will result in low moisture vapor transmission through the patch. This configuration may also be used with other medicaments.

The thermoplastic, water-soluble polymers that are useful in this invention are selected from pharmaceutical grade materials, or those that are considered "generally regarded as safe" (GRAS) as food additives. They include, hydroxypropyl cellulose, and polyethylene oxide homopolymers and copolymers. The term "thermoplastic" as used herein indicates that the polymers are adequately rigid at normal temperatures and under normal conditions of stress, but are capable of deformation under heat and pressure. The term "water-soluble" as used herein indicates that the thermoplastic polymers are soluble or swellable in aqueous or aqueous-based solutions. Hydroxypropyl cellulose has an added advantage; namely, it is also soluble in non-aqueous solvents like methanol.

The compositions of the invention comprise about 5–70% of thermoplastic, water-soluble polymer, preferably about 10–40%, more preferably about 10–30%, even more preferably about 20–30% and most preferably about 23–30%.

Preferably, the thermoplastic, water-soluble polymers of the invention consist essentially of hydroxypropyl cellulose and/or polyethylene oxide. Thus, the hydroxypropyl cellulose and polyethylene oxide polymers useful for this invention can be used singly or a mixture. If a mixture of hydroxypropyl cellulose and polyethylene oxide is used, preferably they are used in a ratio of between about 1:9 to about 9:1, by weight, more preferably between about 4:6 to about 4:0, even more preferably at ratio of about 4:1.

The hydroxypropyl cellulose ("HPC") useful for purposes of the present invention is commercially available from Aqualon, Inc. (Wilmington, Del.) under the trade name KLUCEL®. Preferred grades include KLUCEL EF, with an average molecular weight of about 60,000 and having a viscosity of about 300–700 cps (Brookfield) in a 10 percent water solution, or KLUCEL LF, with a molecular weight of about 100,000 and having a viscosity of about 75–150 cps in a 5 percent water solution. In general, any HPC having a number average molecular weight above about 60,000 is useful for purposes of this invention.

The homopolymer of ethylene oxide useful for purposes of this invention has a number average molecular weight of between about 100,000 to 3,000,0000 or even higher. Although polyethylene oxide ("PEO") polymers having an average molecular weight of above 600,000 are useful for several embodiments of the invention, PEO having a number average molecular weight of less than about 600,000 is preferred, less than about 400,000 is more preferred, and between about 100,000 and 400,000 is even more preferred. Such polymers are commercially available from the Union Carbide Corporation under the trade name POLYOX. Preferred grades include POLYOX WSR-N-10, which has an average molecular weight of about 100,000 and POLYOX WSR-N8, which has an average molecular weight of about 200,000.

Small amounts of other (non-thermoplastic or thermoplastic) water-soluble polymers may be used as well, replacing a small portion of the water-soluble, thermoplastic polymers. Other polymers which are useful for the present invention include, for example, homopolymers and copolymers of carboxymethyl cellulose, hydroxyethyl cellulose, polyacrylamide, polyacrylic acid and its homologs, polyvinyl alcohol, polyvinyl pyrrolidone, polyethylene amines, polymethacrylic acid, polyvinylamine, polymethacrylamide, polyvinylmethylether, and the like. Natural gums such as polysaccharides, alginates, carrageenan, guar gum, gum agar, gum arabic, gum ghatti, gum karaya, gum tragacanth, locust bean gum, pectins, starch and its derivatives, tamarind gum, and xanthan are also useful. The gums are used to adjust the hydrophilic/hydrophobic balance of the composition, which in turn affects the solubility of the medicament in the composition.

Small amounts of polymers derived from carboxylic acids (or from pharmaceutically acceptable salts thereof) provide increased flexibility and stability to the extrudable compositions of the invention. The carboxylic acid polymers useful for the invention include any such polymer having a number average molecular weight of above about 450,000. Preferably, the compositions of the invention comprise at least one such polymer in amounts of between about 1–10% (by weight), preferably between about 3–8%, and most preferably between about 5–7%.

Homopolymers and copolymers derived from acrylic acid are preferred. Copolymers comprised mainly of acrylic acid and allylsucrose, such as those commercially available from B. F. Goodrich under the trade name CARBOPOL, are even more preferred. For example, CARBOPOL 934P, having a molecular weight of about 3,000,000 is especially preferred. Other polymers that are suitable for the invention include homopolymers and copolymers derived from methyl acrylate, methacrylic acid, methyl methacrylate or hydroxyethyl methacrylate, or their amide derivatives.

Suitable pharmaceutically acceptable salts of the carboxylic acid polymers include alkali metal salts such as sodium or potassium salts and ammonium salts. The degree of neutralization of salts is not limited. The pharmaceutically acceptable salts may have any molecular weight.

Any pharmaceutically acceptable medicament or pharmaceutical agent may be delivered by the drug delivery system of the present invention. Usable medicaments include those which are capable of withstanding the heats and pressures generated in the extrusion process involved in making the films of the present invention.

Preferred medicaments include:

anesthetics and/or analgesics such as benzocaine, lidocaine, dyclonine HCl, phenol, menthol, aspirin, phenacetin, acetaminophen, ibuprofen, potassium nitrate, and the like;

anti-inflammatories such as hydrocortisone acetate, triamcinolone acetonide, glycyrrhizinate, and the like;

antihistamines such as chlorpheniramine maleate, ephedrine HCl, diphenhydramine HCl, and the like;

antibiotics such as tetracycline, doxycycline hyclate, meclocyline, minocycline, bacitracin zinc, polymyxin B sulfate, neomycin sulfate, and the like;

fungistats such as nystatin, miconazole, ketoconazole, and the like;

anti-acne agents like salicylic acid; and antiseptics such as benzylalkonium chloride; iodine, silver solfidiazine, chlorohexidine and salts thereof, cetylpyridinium chloride, and the like.

Medicaments that are not capable of withstanding the heats and pressure generated in the extrusion process are also of use in the present invention. Such medicaments can be applied to the extruded compositions using techniques that are well-known to those skilled in the art. For example, such medicaments may be dissolved in a solvent and coated onto the extruded compositions or films. As the solvent evaporates, it leaves behind the medicament. Anti-acne medicaments like retinoic acid and benzoyl peroxide can be utilized in the present invention in this manner.

The medicament should be added in a pharmaceutically effective amount, i.e., an amount sufficient to prevent, cure or treat a disease to which the pharmaceutical preparation of this invention is to be applied. The compositions of the invention typically comprise at least one medicament, and preferably more than one, in amounts ranging from between about 0.01 to 10%, by weight.

Plasticizers useful for purposes of the present invention include block copolymers of polyethyleneoxide and polypropyleneoxide such as PLURONIC® F 127 and TETRONIC® 1302; glycols such as propylene glycol and polyethylene glycol; polyhydric alcohols such as glycerin and sorbitol; glycerol esters such as glycerol triacetate; fatty acid triglycerides such as NEOBEE® M-5 and MYVEROL®; mineral oils; vegetable oils such as castor oil, and the like. These plasticizers may be used singly or in any combination.

The purpose of the plasticizer is several fold; namely, to improve polymer melt processing by reducing polymer viscosity, to increase adhesion to the skin, to increase the dissolution rate in body fluids, and/or to impart flexibility to the final product. In addition, the plasticizer can impart "ointment-like" characteristics to the final product as defined by U.S.P. "Hydrophilic Ointments or Gels."

Compositions of the invention comprise between about 10–80% (by weight) of plasticizer, preferably between about 30–80%, more preferably between about 30–70%, and most preferably between about 60–70%.

Preferred plasticizers include propylene glycol or polyethylene glycol (PEG) polymers having a number average molecular weight of from about 200 to 20,000. Although PEG polymers having higher average molecular weights are useful in the present invention, such polymers having an average molecular weight between 200 to 3500 are preferred. More preferred are PEG polymers having an average molecular weight of between 200 and 1500, such as CARBOWAX 600 (available from Union Carbide corporation), which has an average molecular weight of about 600. Glycerin (especially Grade 916 USP, available from Emory), is also preferred plasticizer.

In one preferred embodiment of the invention, the extrudable compositions comprise, and preferably consist essentially of:

a. thermoplastic water-soluble polymer;

b. a water-soluble polymer derived from a carboxylic acid or a pharmaceutically acceptable salt thereof;

c. plasticizer; and d. medicament.

The inventors have found that the advantages attained by the novel compositions are due to the unique formulations described herein.

Preferably the compositions of this embodiment comprise about 5–70% of (a), about 1–10% of (b), about 10–80% of (c), and about 0.01–10% of (d), by weight. More preferably, they comprise about 10–40% of (a), about 1–10% of (b), about 30–80% of (c), and about 0.01–10% of (d). Even more preferably, they comprise about 20–30% of (a), about 3–8% of (b), about 30–70% of (c), and about 0.01–10% of (d). Most preferably, the compositions comprise about 23–30% of (a), about 5–7% of (b), about 60–70% of (c), and about 0.01–10% of (d).

In accordance with the teachings above and in another preferred embodiment, the extrudable compositions of the invention comprise about 10–30% of (a), about 1–10% (b), about 60–70% of (c), and about 0.01–10% of (d), by weight.

In yet another embodiment, the compositions of the invention comprise about 20–30% hydroxypropyl cellulose and about 0–10% polyethylene oxide, about 1–10% of a copolymer derived from acrylic acid and allyl sucrose, about 0.01–10% of said medicament, and about 60–70% of glycerin; by weight. Even more preferably, they comprise about 22–29% hydroxypropyl cellulose and about 4–7% polyethylene oxide, about 5–7% of said copolymer, about 0.01–10% of said medicament, and about 60–70% glycerin; by weight.

In yet another embodiment which has been found to be particularly suitable for blemish patches, the extrudable compositions of the invention comprise about 22–27% hydroxypropyl cellulose, about 5–7% of said acrylic acid-allyl sucrose copolymer, about 0.01–10% medicament, and about 60–70% glycerin; by weight. Alternatively, such a composition may comprise about 10–15% hydroxypropyl cellulose and 15–20% polyethylene oxide, about 5–7% of said acrylic acid-allyl sucrose copolymer, about 0.01–10% medicament, and about 30–40% of glycerin and 30–40% polyethylene glycol; by weight.

The inventors have further found that for certain applications that are especially suitable for use with adhesive bandages, the carboxylic acid polymer may be left out of the extrudable composition altogether. In practicing this embodiment of the invention the extrudable composition comprises polyethylene oxide, plasticizer and medicament.

Preferably, the extrudable compositions of this embodiment comprise about 15–80% of polyethylene oxide and about 20–85% of plasticizer, by weight. More preferably they comprise about 25–70% of polyethylene oxide and about 30–75% of plasticizer, by weight. Even more preferably they comprise about 35–60% of polyethylene oxide and about 40–65% of plasticizer, by weight. Of course, about 0–10% (preferably 0.01–10%), by weight, of a medicament can replace the equivalent amount of any of the above ingredients. The preferred plasticizer for use in this composition is polyethylene glycol.

The extrudable compositions of the invention may be prepared by mixing the above ingredients in a variety of ways well-known to those skilled in the art. For example, the preweighed ingredients can be added to an intensive mixer such as a Brabender Prep Center or a Baker Perkins Blender and mixed at 80–95° C., with or without solvent. Thus, the compositions can be prepared as hot melts. Alternatively, aqueous solvents or alcohols (like methanol) can be used.

The resultant blend can be cast at elevated temperatures, at say, about 50 to 140° C. Alternatively, the blend can be extruded using a single or twin extruder, or pelletized. If extruded, film thicknesses may vary from "thin" films of about 1.0 ml to "thick" films of about 20 mils or greater, the thickness depending on the intended use of the product. The film can also be extrusion coated onto a variety of substrates as discussed above and then subjected to heat and pressure to form a laminate. Temperatures on the order of 21°–130° C. and contact pressures of up to 40 pounds per linear inch are suitable for forming the laminate. Additional films or insoluble ingredients, such as a water-insoluble medicaments, may be coated or laminated onto the resultant product.

When used in connection with an absorbent pad, the compositions of the invention may be at least partially impregnated into the absorbent pad using any technique well-known to those skilled in the art. Alternatively, the film or composition can be applied adjacent to the body facing surface of the absorbent pad by the use of elevated temperatures and pressures. In the latter embodiment, the film or composition is distinct or discernable from the underlying absorbent pad.

Moisture sensitive or water-insoluble active ingredients also can be blended into the compositions of the invention without degradation or separation from the solid components, since the remaining components of the extrudable composition are frequently soluble in aqueous and non-aqueous solvents and are also useable as hot melts.

In addition to the polymers and plasticizers, minor amounts of other non-essential but customary ingredients will often be used if desired, e.g., antioxidants, foamers, neutralizing agents, stabilizing agents, fillers, preservatives, flavors, and colorants. For example, the extrudable composition can be modified to impart more or less tack contain a color, or to produce a scent to heighten the sensory cue to the user that the product is working. Another modification includes adding fumed silica to improve absorption and stability of the compositions. The fumed silica is generally added in an amount ranging from about 0.01 to about 5% by weight of the total composition. As another example, sodium bicarbonate and/or citric acid can be added to the compositions to enable them to foam upon contact with moisture. The pH of the extrudable composition is also generally controlled within the range of about 3 to 8.

This invention will now be illustrated in greater detail by reference to the following examples, but it should be understood that they are not intended to limit the present invention. In these examples, all the parts, percents and ratios are by weight unless otherwise indicated.

EXAMPLE 1

An ointment film was formed by adding 100 gms of polyethylene oxide (POLYOX N-10) to 200 gms of polyethylene glycol (CARBOWAX 600) in a Brabender heated at 80° C. The components were blended for five minutes to fully plasticize the polyethylene oxide. Then, 26 gms of copolymer of acrylic acid and allyl sucrose (CARBOPOL 934P), was slowly added to the blend and mixed for an additional 30 minutes. The resultant ointment was extrusion coated onto unitized pad stock to form a flexible, aesthetically pleasing film.

EXAMPLE 2

Various antibiotics and antiseptics were added to the composition of Example 1 at the concentrations shown below. The resulting compositions were then coated onto pad stock to form a film layer.

| Sample | Antibiotic/Antiseptic | Concentration |
|---|---|---|
| A | Bacitracin Zinc[1] | 500 units/gm |
|   | Neomycin Sulfate[2] | 3.5 mg/mg |
|   | Polymyxin B Sulfate[3] | 10,000 units/gm |
| B | Neomycin Sulfate[2] | 3.5 mg/mg |
|   | Polymyxin B Sulfate[3] | 10,000 units/gm |
| C | Benzalkonium Chloride | 0.13 (% w/w) |

[1]Activity = 71000 U/gm
[2]Activity = 0.7 gm/gm
[3]Activity = 7700 U/gm

Samples A, B and C were not sterilized.

Additional samples were prepared as follows:

Sample D=Sample A ethylene oxide sterilized at 165° F. (with moisture).

Sample E=The film sample of Example 1 without antibiotics/antiseptics or sterilization.

Sample F=NEOSPORIN Maximum Strength Ointment (Burroughs-Welcome Co.) coated onto filter paper.

Sample G=Untreated filter paper.

Sample A–G were then tested to determine their antimicrobial activity using the zone of inhibition method. Agar base layers were poured into petri dishes and allowed to solidify. The base layers were then covered with a seeded (inoculated) agar layer. The seeded agar layer contained three test microorganisms *Staphylococcus epidermidis*, *Micrococcus luteus* and *Bordetella bronchiseptica* (evaluated separately) as recommended in the USP Pharmacopeia XXII for testing neomycin, bacitracin and polymyxin, respectively.

Pieces of each of the Samples (8 sq. mm) were placed active side down on each seeded agar plate (6 squares were evaluated per test organism). The samples were incubated at 35° C. for 18 hours. The clear zones of inhibition were measured and are reported below as the average of the six zones:

| | Clear Zone in Millimeters | | |
|---|---|---|---|
| Sample | M. luteus | S. epidermidis | B. bronchiseptica |
| A | 11.7 | 11.0 | 11.7 |
| B | 0.0 | 11.2 | 11.7 |
| C | 17.2 | 16.0 | 4.0 |
| D | 5.8 | 10.5 | 10.7 |
| E | 0.0 | 0.0 | 0.0 |
| F | 10.5 | 14.2 | 7.5 |
| G | 0.0 | 0.0 | 0.0 |

The above results demonstrate that the compositions of the present invention (Samples A–D) exhibit good antimicrobial activity.

EXAMPLE 3

Approximately 0.5% (by weight) of fumed silica (CABOSIL M-5) was added to the composition of Example 1. The fumed silica is added to moisture-sensitive active-containing films to absorb moisture and improve the stability of the films.

EXAMPLE 4

Approximately 100 gms of sodium bicarbonate and 50 gms of citric acid were added to the ointment blend of Example 1 (after the addition of the copolymer of acrylic acid and ally sucrose) and the blend was mixed for an additional 10 minutes. The resulting film foamed effervescently upon contact with water.

EXAMPLE 5

Blemish Patch

Two extrudable compositions were prepared. Both vehicles were anhydrous, hydrophilic blends made from the following raw materials:

| | Low Tack Vehicle | High Tack Vehicle |
|---|---|---|
| Acrylic Acid - Ally Sucrose Copolymer (CARBOPOL 934P) | 5.6% | 6.2% |
| Polyethylene Glycol (CARBOWAX 600) | 32.3% | 0 |
| GLYCERIN (USP 99.5%) | 32.3% | 67.0% |
| Hydroxypropyl Cellulose (KLUCEL EF) | 11.1% | 24.8% |
| Polyethylene Oxide (POLYOX N-10) | 16.7% | 0 |
| Salicylic Acid | 2.0% | 2.0% |

Mixing was performed in a Baker-Perkins Blender at a screw speed of 30 RPM, blade speed of 36 RPM, at 80° C. for about 30 minutes. The polyethylene glycol and/or glycerin were premixed and then added to the mixing bowl of the blender. The hydroxypropyl cellulose, acrylic acid-allyl sucrose, copolymer and polyethylene oxide (low tack only) were also premixed in a "V" blender for about three and a half minutes. After approximately two-three minutes, the premixed powders were added at once to the mixing bowl. The viscosity of the blend quickly increased and began generating sheer force. The blend was masticated for about twenty-five minutes and then salicylic acid was added.

Pelletizing the Ointment

After mixing for about thirty minutes (total mixing time), the blend was extruded as a rod directly into the pelletizer. (Prior to reaching the pelletizer, a cooling stage may be added to ensure a solidified ointment.) The pellets had a diameter of approximately ¼" or less.

Extruding the Ointment

A Killian extruder was used for extrusion. Initial settings were as follows:

| ZONE 1 | ZONE 2 | ZONE 3 | ZONE 4 | DIE |
|---|---|---|---|---|
| 150° F. | 160° F. | 175° F. | 180° F. | 200° F. |
| SCREW SPEED | LINE SPEED | | | |
| 50 RPM | 21 FT/MIN | | | |

The extruded film was laminated to two substrates; clear unitized pad stock used in BAND-AID® brand adhesive bandages and flexible fabric. (The roll may require a silicone release sheet as a carrier paper.) No finishing was required.

EXAMPLE 6

Rheological Data

FIG. 1 is a graph showing the relationship between viscosity and temperature of a composition of the present invention (Composition A) and a composition from EP Application No. 0297828 to Charkondian et al. (Composition B). The viscosity is reported in poises.

Composition A was prepared and then extruded into a film. Composition B was prepared in accordance with Example 2 of EP Application No. 0297828, except that benzocaine was omitted, and the viscosity was measured after the methanol solvent was removed.

Composition A (weight %)

Acrylic Acid-Allyl Sucrose Copolymer—6.42% (CARBOPOL 934P)

Hydroxypropyl Cellulose—25.7% (KLUCEL EF NF)

Glycerine—65.78%

Potassium Hydroxide (dry)—2.0%

Fumed Silica (CABOSIL M-5)—0.1%

Dye—trace amount

Composition B

Polyvinylpyrrolidone—40 gms.

Polyethylene Glycol 400—60 gms.

Methanol—125 ml.

The viscosity of Compositions A and B was measured on a Rheometrics RDS-7700 parallel plate rheometer at 10 rad./sec. The resulting data is shown on FIG. 1. Since the composition of the present invention is more viscous, it will be more resistant to flow than the composition of EP Appln. No. 0297828. This is an important property of the composition of the present invention, since it is not desirable to have the film and resulting medicament flow from the bandage or the traumatized area of the skin to which it is applied.

EXAMPLE 7

An additional extrudable composition suitable for use in a blemish pad was prepared using procedures similar to those described in Example 5. The composition contained (weight%):

Glycerine—53%

Acrylic Acid—Ally Sucrose Copolymer (CARBOPOL 934P)—6%

Hydroxypropyl Cellulose (KLUCEL EF NF)—26%

Fumed Silica (CARBOSIL M-5)—1%

Salicylic Acid—2%

Na—Ca Salt of Polyvinyl Menthyl Ether Maleic Anhydride (GANTREZ MS-955)—12%

EXAMPLE 8

A composition was prepared by blending 28% polyethylene oxide (POLYOX N-80) (having an average molecular weight of about 200,000) with 72% polyethylene glycol (CARBOWAX 600), in a Brabender mixer for one hour at 80° C. The blend was coated onto release paper and laminated at 60° C. onto unitized pad stock. The resultant films had thicknesses of between 1 to 3 ounces/yd$^2$. The films did not interfere with the conventional absorption of the pad stock, and did not flake or peel.

EXAMPLE 9

Blends of polyethylene glycol (PEG) (number average molecular weight of between 200–1450) and polyethylene oxide (PEO) (number average molecular weight of approximately 100,000) having the proportions shown below were prepared and laminated onto unitized pad stock using procedures similar to those described in Example 8.

| Sample | PEG | PEO (% W/W) |
|---|---|---|
| A | 51 | 49 |
| B | 62.5 | 37.5 |
| C | 25 | 75 |
| D | 83.3 | 16.7 |
| E | 5 | 95 |
| F | 86 | 14 |

The films were evaluated for their flexibility, dissolution rate and stability at elevated temperatures and humidity. Samples A and B were preferred because they exhibited good flexibility and dissolution rates. Samples C and D had acceptable properties, and Samples E and F were found to have unacceptable properties.

EXAMPLE 10

When the medicament is heat or pressure sensitive, composition of the invention can be blended without medicament, and extrusion coated onto a substrate. Then, the medicament can be deposited onto the film using any technique well-known to those skilled in the art. The following is an example of this technique.

Layer 1 have the composition shown below was blended and extrusion coated onto flexible fabric using procedures similar to those described in Example 5.

| Layer 1 | wt % |
|---|---|
| Acrylic Acid - Allyl Sucrose Copolymer (CARBOPOL 934P) | 6.5 |
| Glycerin (Emory 916 USP) | 54.5 |
| Hydroxypropyl Cellulose (KLUCEL JF EF) | 26.0 |
| Fumed Silica (Cabosil M-5) | 1.0 |
| Na-Ca Salt of a Copolymer of Polyvinyi Menthyl Ether and Maleic Anhydride (GANTREZ MS-955) | 12.0 |

A solution of benzoyl peroxide was prepared by mixing the composition shown below with an equal amount (by weight) of acetone. This solution was then coated onto Layer 1. Layer 2 was dried and the acetone was allowed to evaporate, which resulted in a tacky benzoyl peroxide-containing layer laminated to Layer 1. The resulting structure is suitable for use as a blemish patch.

| Layer 2 | wt % |
|---|---|
| Benzoyl Peroxide | 10.0 |
| Dimethylaminoethyl Methacrylate | 65.0 |
| Triacetine | 25.0 |

Additional solvents may be added to enhance solubility. However, any solvent used must have a low boiling point and high vapor pressure to ensure that critically high temperatures are not reached during the drying step.

EXAMPLE 11

Examples of Multilayered Films

A single-layered film containing the medicament "A" is made in accordance with the present invention, and is extruded onto a substrate. A second extruded film containing medicament "B" is then extruded onto the first layer. Thus, the "B-containing" film is in contact with the skin and "B" is the first medicament that comes in contact with the inflamed skin or wound. For example, the B-containing film may contain lidocaine for pain relief and the A-containing film may contain hydrocortisone for reducing inflammation. Additional film laminates containing many separate drug layers and different medication strategies can be constructed.

Diffusion of the "bioactive-type" drugs typically occurs at skin temperature, e.g., 33 to 35° C. In order to minimize transfer or co-mingling of drugs between separate film layers, the compositions can be stored under cold conditions (say, for example, at approximately 4° C.) and brought to room temperature when needed.

Various modifications can be made to the above-described embodiment without departing from the spirit and scope of the present invention.

What is claimed is:

1. A composition comprising:
   a. about 10–40% by weight of a thermoplastic water-soluble polymer;
   b. about 1–10% by weight of a water-soluble polymer derived from a carboxylic acid or a pharmaceutically acceptable salt thereof;
   c. about 30–80% by weight of a plasticizer; and
   d. about 0.01–10% by weight of a medicament.

2. The composition of claim 1 wherein (a) comprises at least one polymer selected from the group consisting of hydroxypropyl cellulose and polyethylene oxide.

3. The composition of claim 2 wherein said polyethylene oxide has a number average molecular weight of greater than about 600,000.

4. The composition of claim 2 wherein said polyethylene oxide has a number average molecular weight of less than about 600,000.

5. The composition of claim 2 wherein said polyethylene oxide has a number average molecular weight of between about 100,000 and 400,000.

6. The composition of claim 2 wherein said hydroxypropyl cellulose has a number average molecular weight greater than about 60,000.

7. The composition of claim 1 wherein (b) is polyacrylic acid.

8. The composition of claim 1 wherein (d) is at least one medicament selected from the group consisting of analgesics, anti-inflammatories, antihistamines, antibiotics, anesthetics, antiseptics, fungistats and anti-acne agents.

9. The composition of claim 1 wherein (d) is at least one medicament selected from the group consisting of antibiotics and antiseptics.

10. The composition of claim 1 wherein (d) is at least one medicament selected from the group consisting of benzalkonium chloride, bacitracin zinc, polymyxin B sulfate, and neomycin sulfate.

11. The composition of claim 1 wherein (d) is at least one anti-acne agent selected form the group consisting of salicylic acid, benzoyl peroxide, retinoic acid and pharmaceutically derivatives thereof.

12. The composition of claim 1 wherein (c) is at least one plasticizer selected from the group consisting of glycerin, propylene glycol and polyethylene glycol.

13. The composition of claim 12 wherein said polyethylene glycol has a number average molecular weight of between about 200 to 20,000.

14. The composition of claim 12 wherein said polyethylene glycol has a number average molecular weight of between about 200 to 1500.

15. The composition of claim 1 which is extruded into a single or multilayered film.

16. The composition of claim 1 wherein said medicament is homogeneously blended with (a), (b) and (c).

17. The composition of claim 1 wherein said medicament is coated onto a mixture of (a), (b) and (c).

18. A composition comprising:
   a. about 20–30% by weight of hydroxypropyl cellulose and about 0–10% of polyethylene oxide;
   b. about 1–10% by weight of a copolymer of acrylic acid and allyl sucrose;
   c. about 60–70% by weight of glycerin; and
   d. about 0.01–10% by weight of a medicament.

19. The composition of claim 18 comprising:
   a. about 22–27% of said hydroxypropyl cellulose and about 4–7% of said polyethylene oxide;
   b. about 5–7% of said copolymer;
   c. about 60–70% of said glycerin; and
   d. about 0.01–10% of said medicament, by weight.

20. The composition of claim 18 comprising:
   a. about 22–27% hydroxypropyl cellulose;
   b. about 5–7% of said copolymer;
   c. about 60–70% glycerin; and
   d. about 0.01–10% medicament, by weight.

21. A bandage comprising an absorbent pad and a composition, said composition comprising:
   a. a thermoplastic water-soluble polymer;
   b. a water-soluble polymer derived from a carboxylic acid or a pharmaceutically acceptable salt thereof;
   c. a plasticizer;
   d. a medicament; and
   e. silica.

22. The bandage of claim 21 comprising about 5–70% of (a), about 1–10% of (b), about 10–80% of (c), and about 0.01–10% of (d), by weight.

23. The bandage of claim 21 wherein (a) comprises at least one polymer selected from the group consisting of hydroxypropyl cellulose and polyethylene oxide.

24. The bandage of claim 21 wherein (b) is polyacrylic acid.

25. The bandage of claim 21 wherein (b) is a copolymer of acrylic acid and allyl sucrose.

26. The bandage of claim 21 wherein (c) is at least one medicament selected from the group consisting of analgesics, anti-inflammatories, antihistamines, antibiotics, anesthetics, antiseptics, fungistats and anti-acne agents.

27. The bandage of claim 21 wherein (d) is at least one plasticizer selected from the group consisting of glycerin, propylene glycol and polyethylene glycol.

28. The bandage of claim 21 wherein the composition is an extruded film disposed on said absorbent pad.

29. The bandage of claim 28 further comprising a backing film and an adhesive, and said pad is disposed on said backing film.

30. The bandage of claim 29 wherein said composition is disposed on the skin facing surface of said pad.

31. The bandage of claim 21 wherein said medicament is homogeneously blended with (a), (b), and (c).

32. The bandage of claim 21 wherein said medicament is coated onto a mixture of (a), (b), and (c).

33. A composition comprising:
 a. a thermoplastic water-soluble polymer;
 b. a water-soluble polymer derived from a carboxylic acid or a pharmaceutically acceptable salt thereof;
 c. a copolymer of acrylic acid and allyl sucrose as a plasticizer; and
 d. a medicament.

34. A composition comprising:
 a. at least one thermoplastic water-soluble polymer selected from the group consisting of hydroxypropyl cellulose and polyethylene oxide;
 b. a water-soluble polymer derived from acrylic acid or a pharmaceutically acceptable salt thereof;
 c. a plasticizer; and
 d. a medicament.

35. A composition comprising:
 a. a thermoplastic water-soluble polymer;
 b. a water-soluble polymer derived from acrylic acid or a pharmaceutically acceptable salt thereof;
 c. a plasticizer;
 d. a medicament; and
 e. silica.

36. A composition comprising:
 a. about 10–15% by weight of hydroxypropyl cellulose and 15–20% of polyethylene oxide;
 b. about 5–7% by weight of a copolymer of acrylic acid and allyl sucrose;
 c. about 30–40% by weight of glycerin and 30–40% of polyethylene glycol; and
 d. about 0.01–10% by weight of a medicament.

37. A method of delivering a medicament to a wound comprising applying to said wound a composition comprising:
 a. about 35–60% by weight of polyethylene oxide;
 b. a water-soluble polymer derived from a carboxylic acid or a pharmaceutically acceptable salt thereof;
 c. about 40–65% by weight of polyethylene glycol; and
 d. about 0.01–10% by weight of a medicament.

38. A composition comprising:
 a. about 23–30% by weight of a thermoplastic water-soluble polymer;
 b. about 5–7% by weight of a water-soluble polymer derived from a carboxylic acid or a pharmaceutically acceptable salt thereof;
 c. about 60–70% by weight of a plasticizer; and
 d. about 0.01–10% by weight of a medicament.

39. A composition comprising:
 a. a thermoplastic water-soluble polymer;
 b. a water-soluble polymer derived from acrylic acid or a pharmaceutically acceptable salt thereof, said polyacrylic acid polymer having a number average molecular weight greater than about 450,000;
 c. a plasticizer; and
 d. a medicament.

* * * * *